United States Patent [19]

Cohen et al.

[11] Patent Number: 4,991,603

[45] Date of Patent: Feb. 12, 1991

[54] TRANSVENOUSLY PLACED DEFIBRILLATION LEADS VIA AN INFERIOR VENA CAVA ACCESS SITE AND METHOD OF USE

[75] Inventors: Donald M. Cohen, Irvine; Werner Hafelfinger, Valencia, both of Calif.

[73] Assignee: Siemens-Pacesetter, Inc., Sylmar, Calif.

[21] Appl. No.: 429,261

[22] Filed: Oct. 30, 1989

[51] Int. Cl.⁵ .............................................. A61N 1/05
[52] U.S. Cl. .................................. 128/786; 128/419 D
[58] Field of Search ............ 128/784, 785, 786, 419 D; 606/1

[56] References Cited

U.S. PATENT DOCUMENTS

| | | | |
|---|---|---|---|
| 3,866,615 | 2/1975 | Hewson | 128/419 D |
| 3,942,536 | 3/1976 | Mirowski et al. | 128/419 D |
| 4,030,509 | 6/1977 | Heilman et al. | 128/419 D |
| 4,161,952 | 7/1979 | Kinney | 128/786 |
| 4,270,549 | 6/1981 | Heilman | 128/784 |
| 4,291,707 | 9/1981 | Heilman et al. | 128/784 |
| 4,351,345 | 9/1982 | Carney | 128/786 |
| 4,355,646 | 10/1982 | Kallok et al. | 128/786 |
| 4,548,203 | 10/1985 | Tacker, Jr. et al. | 128/419 D |
| 4,567,900 | 2/1986 | Moore | 128/784 |
| 4,603,705 | 8/1986 | Speicher et al. | 128/786 |
| 4,628,937 | 12/1986 | Hess et al. | 128/642 |
| 4,641,649 | 2/1987 | Walinsky et al. | 128/784 |
| 4,641,656 | 2/1987 | Smits | 128/419 D |
| 4,662,377 | 5/1987 | Heilman et al. | 128/419 D |
| 4,815,469 | 3/1989 | Cohen et al. | 128/634 |

Primary Examiner—William E. Kamm
Attorney, Agent, or Firm—Bryant R. Gold; Lisa P. Weinberg; Leslie S. Miller

[57] ABSTRACT

A method and system for positioning a defibrillation electrode about the heart includes means for placing the electrode in contact with epicardial or pericardial tissue from an inferior vena cava (IVC) access site. A small hole is made in the IVC at the selected access site. A defibrillation lead having the defibrillation electrode near its distal end is transvenously inserted through the IVC and out through the small hole into a chest cavity adjacent the heart. The electrode is then positioned so as to contact the desired cardiac tissue. If pericardial contact is to be made, the distal end of the lead, including the electrode, is looped around the pericardium. If epicardial contact is to be made, an additional small hole is made in the pericardium, and the distal end of the lead, including the electrode, is inserted through the additional hole into the pericardial space, and the electrode is positioned to contact the desired epicardial tissue.

34 Claims, 5 Drawing Sheets

TRANSVENOUSLY PLACED DEFIBRILLATION LEADS VIA AN INFERIOR VENA CAVA ACCESS SITE AND METHOD OF USE

BACKGROUND OF THE INVENTION

The present invention relates to implantable defibrillation leads and electrodes, and more particularly to methods for the transvenous placement of defibrillation electrodes.

A defibrillation device provides an electrical stimulus to a patient in an area near, on or in the heart for the purpose of reviving a heart that is not beating in a manner sufficient to support life. While there are numerous medical terms that can be used to describe such a heart, such as cardiac arrest, ventricular fibrillation, and asystole, and while each term has a somewhat different technical meaning, all are serious conditions that must be corrected immediately to prevent death of the patient. Hence, a defibrillation device is used in an attempt to get the heart beating again. To this end, a high energy stimulation pulse is delivered to or near the heart through one or more defibrillation leads, each lead having one or more electrodes at the distal end thereof. The present invention is concerned primarily with defibrillation leads, and with a manner of positioning the electrodes of such leads on or near the heart so that they can provide the greatest benefit.

Early defibrillation devices were large and cumbersome units that included a set of paddles, connected to a source of stored electrical energy through large wires. The paddles were positioned on the chest of the patient, typically by a doctor or paramedic, and the stored electrical energy was discharged one or more times through the paddles into the patient's body tissue. While such large defibrillation devices provided, and continue to provide, a measure of life support in emergency situations, such support can only be provided if a physician or paramedic having access to such a device is present.

It was recognized early that a defibrillation device could be carried by the patient at all times, i.e., the defibrillation device could be made portable and adapted to respond automatically to a stopped heart. With such a portable device, the needed life-sustaining defibrillation pulses could be automatically provided to the patient even in the absence of a physician or paramedic. One such early portable defibrillation device is disclosed in U.S. Pat. No. 3,866,615. The '615 patent teaches a light weight, portable cardiac emergency stimulator that includes separate defibrillation and pacemaker electronic circuits. The leads and electrodes used with the portable device are introduced into the patient's heart by a needle through the chest wall.

Implantable defibrillation devices have also been developed, as shown in U.S. Pat. No. 3,942,536. Such devices offer the advantages of the portable device without the need for introducing leads through the chest wall. In the '536 patent, defibrillation leads having endocardial electrodes are introduced transvenously into the inside of the heart, similar to the leads used by implantable pacemakers. Other attempts at using transvenous defibrillation leads having endocardial electrodes have also been made, as shown for example in U.S. Pat. Nos. 4,161,952 and 4,355,646.

The advantages of providing an implantable automatic defibrillator in certain patients at high risk of experiencing ventricular fibrillation or other heart disorders are thus readily apparent. When fibrillation or related heart malfunctions are sensed by such devices, a large defibrillation shock is automatically delivered to the heart in an attempt to stimulate the heart back to a normal or near normal beating pattern. The life-saving defibrillation shocks are delivered without any undue delay, as would otherwise exist if external defibrillation pulses had to be delivered by paramedics (or other medical personnel) who were summoned to the aid of a heart-failing patient.

One of the main problems associated with defibrillating a heart (replacing a dangerous rhythm with a more normal one) with an electrical stimulus, however, is that a relatively large surface area of the myocardial tissue, typically ventricular myocardial tissue, must be stimulated in order to overcome fibrillation. This problem is compounded by the fact that the myocardium, which comprises mostly cardiac muscle, is the middle of three layers of tissue that comprise the heart wall, the inner layer being termed the endocardium, and the outer layer being termed the epicardium. Hence, the myocardium is generally not directly accessible with a defibrillation electrode. Rather, the defibrillation pulse (electric field potential) must pass through one or more layers of other tissue before reaching the myocardial muscle tissue that needs to be depolarized (excited). Some of the energy is naturally expended on body fluids and tissues other than the myocardium. Hence, more energy must usually be delivered over a larger tissue area than would otherwise be required if the myocardial tissue were more directly accessible.

Prior art defibrillation leads and electrodes have generally been concerned with the size and shape of the surface area of the electrodes and correctly positioning the electrodes relative to the heart. Typically, at least a pair of such electrodes are positioned on or in the patient so that the defibrillating electrical energy passes through the appropriate myocardial tissue and the amount of energy delivered to other tissues is minimized. U.S. Pat. Nos. 4,030,509; 4,291,707; and 4,548,203 are representative of such efforts. Unfortunately, placement of relatively large electrodes on the exterior of the heart, i.e., epicardial electrodes, has usually required open chest surgery—a difficult and somewhat risky procedure at best. Placement of large electrodes on the interior of the heart, i.e., endocardial electrodes, is not easy without open-heart surgery—an even more difficult and risky procedure. Furthermore, placement of large electrodes within the heart may impair cardiac function and/or contribute to thrombosis or emboli formation in the left heart.

One problem associated with placement of epicardial defibrillation electrodes is that the heart resides in the pericardium. The pericardium is a membranous sac that encloses the heart. It consists of an outer layer of dense fibrous tissue, with an inner serous layer (the epicardium) which directly surrounds the heart. While it is possible, and sometimes preferred, to place defibrillation electrodes external to the pericardium, such placement typically requires an increased defibrillation energy as the electrical stimulus must pass through the pericardium and epicardium (and any other tissue in the electrical path) before reaching the myocardium. Hence, the amount of defibrillation energy required can be reduced somewhat if direct contact is made between the defibrillation electrode and epicardial tissue. However, before such direct contact can be made, the pericardium must somehow be pierced. Again, this has usually required open-chest surgery, although other techniques for gaining access to the heart have been proposed. See, e.g., U.S. Pat. No. 4,270,549; and applicant's copending U.S. patent application, "Sub-Xiphoid Positioning of Epicardial Defibrillation Electrodes and Electrode Anchoring Means," filed Apr. 4, 1989, as Ser. No. 07/333,391, which application is incorporated herein by reference.

Because of the problems associated with placement of epicardial electrodes, the concept of a transvenously implanted defibrillation lead and endocardial electrode remains an attractive alternative to open-chest surgery. Unfortunately, to date transvenous placement of defibrillation leads and electrodes (acting alone or in concert with subcutaneous electrodes) has proven unsatisfactory because the electrode surface area can not be made large enough for energy efficient cardiac defibrillation. Most prior uses of transvenous defibrillation leads with their resulting endocardial electrodes have thus been limited to uses in combination with epicardial electrodes, as shown for example in U.S. Pat. No. 4,641,656. (In this regard, it should be noted that the amount of energy required to defibrillate a typical fibrillating heart is much larger than the energy required to stimulate a non-fibrillating heart, as is used for example, by a pacemaker.) What is needed, therefore, is a technique for transvenously placing defibrillation leads having epicardial or pericardial electrodes thereby avoiding the trauma and potential problems of open chest surgery.

As indicated above, epicardial electrodes ar generally preferred because their use generally minimizes the energy of a defibrillation pulse, and thereby improves the efficacy of the defibrillation system. Epicardial electrodes are in direct contact with the heart tissue. Further, epicardial electrodes cover large and strategic areas of the heart, thereby allowing the delivered electrical energy to be efficiently distributed throughout the fibrillating region. Such epicardial electrodes are typically placed around the exterior of the heart within the pericardial space. Although there are some shortcomings associated with placement of defibrillation electrodes directly on the epicardial surface, the advantages are overwhelming.

In some situations, it may be preferred to place the electrodes on the outer surface of the pericardium, thereby avoiding the necessity of piercing the pericardium. While the energy delivered by such pericardial electrodes must pass through one additional layer of tissue (the pericardium), the pericardial electrodes are, in most other respects, just as advantageous as the epicardial electrodes. Because of the large surface area covered by many of these electrodes, they are sometimes referred to as "patch electrodes", often resembling patches that are placed on the heart.

Unfortunately, however, as has been indicated, pericardial or epicardial placement of defibrillation leads is a dangerous and difficult procedure that has heretofore generally required traumatic and endangering surgery, usually open-chest surgery. Needless to say, not all patients are suitable candidates for open-chest surgery, and even for those that are, the risks, trauma, and danger associated with such surgery make this procedure of electrode placement less than ideal. Hence, there is a need, as indicated above, for placement of pericardial electrodes on the pericardium, or for the placement of epicardial electrodes in the propitious pericardial space, without having to resort to dangerous open-chest surgery.

In an attempt to minimize the problems associated with open-chest surgery for the placement of epicardial defibrillation leads, it has been suggested to implant epicardial defibrillation leads transvenously. Such an approach is described in patent application Ser. No. 07/128,326, filed 12/03/87, now U.S. Pat. No. 4,884,567, entitled "Method for Transvenous Implantation of Objects into the Pericardial Space of Patients," of which the applicant named herein is a co-inventor. This prior application, including the methods and leads described therein (hereafter referred to as the "transvenous implantation approach"), is incorporated by reference herein.

In accordance with the transvenous implantation approach described in the abovereferenced prior application, a guide wire and a catheter are inserted into the heart transvenously, with the aid of an introducer, as required. Once in the heart, the right atrial lateral wall is punctured, making a hole therein, through which a non-deployed defibrillation electrode is inserted, thereby entering the pericardial space. The nondeployed electrode is further positioned within the pericardial space to a desired position, and then the electrode is deployed so as to better contact a larger surface area of the outside of the heart.

The transvenous implantation approach described in referenced document offers a very viable alternative to open chest surgery for many patients. However, for other patients, the risks and trauma associated with puncturing through the atrial wall, even though less than the risks and trauma associated with open-chest surgery, may not be acceptable, either because of the actual risks for a particular patient or because of the perceived risks. Hence, what is needed is a technique for placing pericardial or epicardial electrodes that not only avoids the need for dangerous open-chest surgery, but that also eliminates the risk and trauma that may accompany atrial puncture. The present invention advantageously addresses these and other needs.

SUMMARY OF THE INVENTION

The present invention is directed to a method and system for positioning an epicardial or pericardial defibrillation electrode(s) about the heart from an IVC (inferior vena cava) access site. A small hole is made in the IVC at a selected access site using conventional tissue coring or puncturing techniques, which techniques minimize the amount of bleeding. A defibrillation lead having the defibrillation electrode(s) near its distal end is then transvenously passed through the IVC and guided out through the small hole into the mediastinum (chest cavity where the heart is located). The electrode is then moved and positioned within the mediastinum so as to be in close proximity to the desired cardiac tissue. If pericardial contact is to be made, the distal end of the lead, including the electrode, is looped around the pericardium using conventional lead positioning means (e.g., stylet and fluoroscope). If epicardial contact is to be made, an additional small hole is made in the pericardium, and the distal end of the lead, including the electrode, is inserted through the additional hole into the pericardial space, and the electrode is positioned to contact the desired epicardial tissue. Suitable guide means, such as a catheter and/or a stylet, are used to assist in the placement and positioning process.

Advantageously, the method and system of the present invention avoids the need for traumatic and dangerous open-chest surgery, as the leads and electrodes are inserted transvenously. Further, the method and system significantly reduces risks attending the implant procedure over those present in the atrial access approach of the prior art, as the integrity of the cardiac tissue is not compromised. That is, the system and method does not use an access path that passes from the inside of the heart to the outside of the heart as taught in the transvenous implantation approach described above, which access path disadvantageously requires making a hole in the atrial wall (atriotomy) through which the lead passes.

Because of the reduced risks associated with the present invention, the morbidity and mortality associated with the defibrillation lead implantation are greatly reduced. Even if a catastrophe does occur, resulting in massive bleeding, such bleeding should occur into the pleural cavity or mediastinum rather than within the pericardium. The effects of massive bleeding in the pleural cavity are not immediately life-threatening. Such effects would probably be limited to pulmonary edema (excessive accumulation of fluid in the chest cavity) and/or reduced hematocrit (reduction in the volume of red blood cells in the vasculature). The former can be treated through chest tube drainage, and the latter can be treated by transfusion. In any event, surgery (even if necessary) is not an extreme emergency.

In contrast, if massive bleeding occurs while performing an atriotomy, as is taught in the prior art, the massive bleeding is in the pericardium, and a tamponade (abnormal pressure exerted on the heart due to excess fluid in the pericardium) may result. Death due to tamponade may take only minutes. Hence, this significant life-threatening risk, which is present in the prior art transvenous implantation approaches where the defibrillation lead and electrode must pass through a hole in the atrial wall, may advantageously be avoided through use of the present invention.

The present invention may be characterized as a method of transvenously implanting a defibrillation lead about a mammalian heart, where the heart is located within a chest cavity of the mammal, and the heart has a major vein proximate thereto. In accordance with this method, the defibrillation lead has at least one distal electrode, a flexible body, and proximal connection means for making electrical contact with the distal electrode from a proximal end of the lead. The method comprises the steps of: (a) transvenously inserting guide means directly into the chest cavity from a position within the major vein; (b) inserting the distal electrode of the defibrillation lead into the chest cavity following the guide means; and (c) positioning the distal electrode within the chest cavity so as to be about the heart. Once the defibrillation lead has been thus implanted, the proximal connection means thereof may be connected to a suitable source of defibrillation energy in order to effectuate defibrillation of the heart.

The present invention may also be characterized as a method of implanting a defibrillation lead about the heart of a patient, the defibrillation lead having at least one exposed conductive surface near its distal end that serves as an electrode, the method comprising the steps of: (a) accessing the inferior vena cava (IVC) of the patient; (b) making a first small hole in the IVC at a location proximate the heart of the patient; (c) inserting the distal end of the defibrillation lead through the first small hole; and (d) positioning the electrode of the defibrillation lead about the heart of the patient.

The invention may still further be characterized as a method of positioning at least one defibrillation electrode about the heart of a mammal, the method including the steps of: (a) inserting the at least one electrode through a vein that passes proximate the heart; (b) routing the at least one electrode through an access site in a wall of the vein to an adjacent chest cavity; and (c) positioning the at least one electrode within the chest cavity so as to make contact with the pericardial tissue. The positioning of the at least one electrode may be either extra-pericardially, in which case the electrode simply makes contact with the pericardial tissue surrounding the heart; or intra-pericardially, in which case the pericardial tissue surrounding the heart is punctured and the electrode is inserted into the pericardium so as to make direct contact with epicardial tissue of the heart.

Still further, the invention may be characterized as a system for implanting a defibrillation lead in a mammal, the mammal having a heart surrounded by a pericardium, the defibrillation lead having at least one flexible elongate electrode near a distal end thereof. This system includes: (a) guide means for transvenously gaining direct access to a chest cavity of the mammal, the heart and pericardium being located within the chest cavity, the direct access passing directly from an access site in a wall of a vein proximate the chest cavity to the chest cavity without substantively passing through the heart; (b) means for inserting the distal end of the lead, including the at least one electrode, into the chest cavity following the guide means; and (c) means for positioning the at least one electrode within the chest cavity about the heart. As with the method of the invention, this system contemplates extra-pericardial and/or intraperi-cardial positioning of the at least one electrode.

Yet another characterization of the invention is a defibrillation lead system that includes: a sheath; means for passing the sheath through to a pericardium surrounding a heart from a position within the inferior vena cava (IVC) adjacent the heart; a defibrillation lead having a distal electrode, the defibrillation lead being of a size that allows it to be slidably inserted through the sheath until the distal electrode is in contact with the pericardium; and holding means for holding the distal electrode in contact with the pericardium. In one embodiment, the holding means includes both stiff and flexible sections of the distal end of the defibrillation lead. The stiff sections allow the distal end of the lead to conform to the basic shape of the heart, just like a basket within which the heart is placed. The flexible sections allow this basic shape to bend, thereby permitting those portions of the lead containing the electrode(s) to remain in contact with the heart tissue even though the heart tissue moves as the heart performs its function of pumping blood.

It is thus a feature of the present invention to provide a simple, safe and efficacious method and system of implanting one or more defibrillation electrodes about the heart.

It is another feature of the invention to provide such a method of epicardial or pericardial defibrillation electrode placement that is less traumatic and less dangerous than prior methods used for this purpose, such as open-chest surgery or transvenous implantation techniques involving an atrial puncture.

It is yet another feature of the invention to provide a defibrillation electrode system that is implanted transvenously and positioned about the heart via an IVC access site.

BRIEF DESCRIPTION OF THE DRAWINGS

The above and other advantages and features of the present invention will be more apparent from the following more particular description thereof, presented in conjunction with the following drawings, wherein.

DETAILED DESCRIPTION OF THE INVENTION

The following description is of the best presently contemplated mode of practicing the invention. This description is not to be taken in a limiting sense but is made merely for the purpose of describing the general principles of the invention. The scope of the invention should be ascertained with reference to the appended claims.

At the outset, it is noted that the drawings used herein are not intended to be fully detailed representations of the physiological makeup of a mammalian heart and its surrounding pericardium, or of any other part or tissue location of the mammal. Rather, all of the drawings are presented in a very simplified format in order to emphasize the main features and steps of the invention. Much physiological detail has been omitted for clarity. However, it also must be emphasized that the drawings have been selected and designed to provide sufficient detail to enable one skilled in the cardiac medical implantation arts to readily carry out and practice the present invention.

Figure 1:
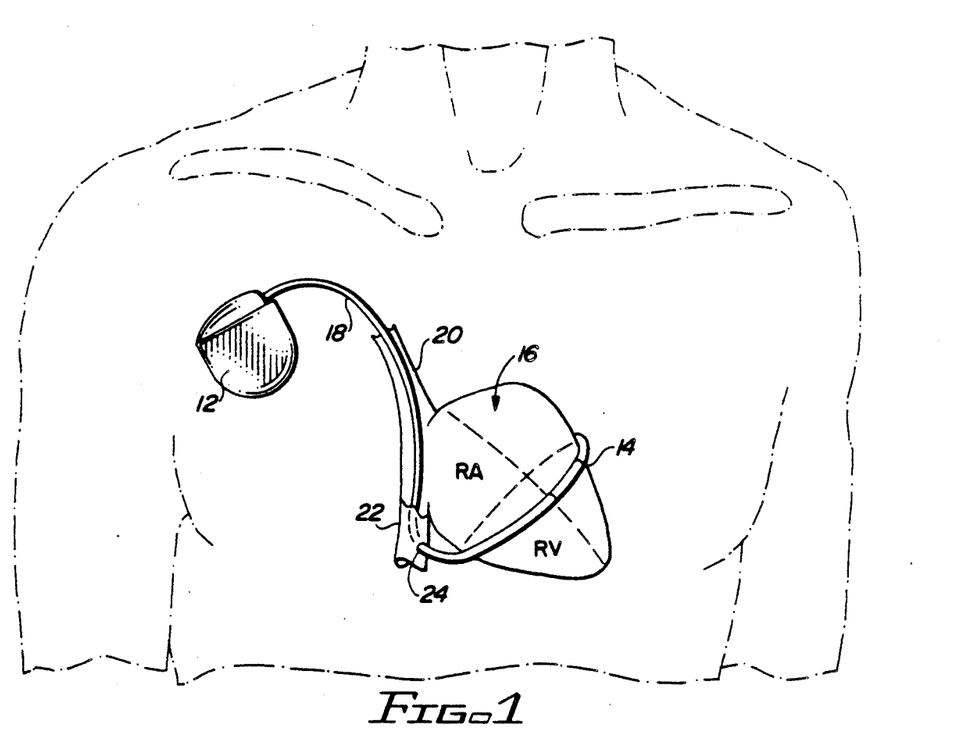
FIG. 1 is a simplified diagram of a human heart, and shows a defibrillation electrode positioned thereon connected to an implanted defibrillation device via a defibrillation lead passing through an IVC access site.

Referring first to FIG. a simplified diagram of one embodiment of the present invention is illustrated. An implantable defibrillation device 12 is connected to one or more defibrillation electrodes 14 in contact with a mammalian heart 16 by way of a defibrillation lead 18. (It is noted that while the heart 16 shown in FIG. 1 is a human heart, this is only exemplary, as the invention could be utilized with any mammalian heart.) The lead 18 passes from the defibrillation device 12, which is implanted in a suitable pocket under the flesh of the mammal in conventional manner, through an appropriate vein to the superior vena cava (SVC) 20 and into the inferior vena cava (IVC) 22. At an appropriate location within the IVC, the lead 18 passes through an opening 24 in the wall of the IVC 18 into the chest cavity where the heart 16 is located. The distal end of the lead 18 is looped around the heart in an appropriate manner so as to place the electrode 14 in contact with the heart at a desired location. The invention thus comprises a defibrillation system wherein the defibrillation lead 18, and its associated electrode(s) 14, are routed to the heart 16 through an access site or hole 24 in the IVC 22. In addition to that which is illustrated in FIG. 1, the invention thus includes any placement of the defibrillation device 12, including external placement, that routes the lead 18 through an access hole 24 in the IVC to the heart 16. For example, the device 12 could be placed near the abdomen, and the lead could be routed to the access hole 24 through the IVC 22 and to the heart, without passing through the SVC 20.

Figure 2:
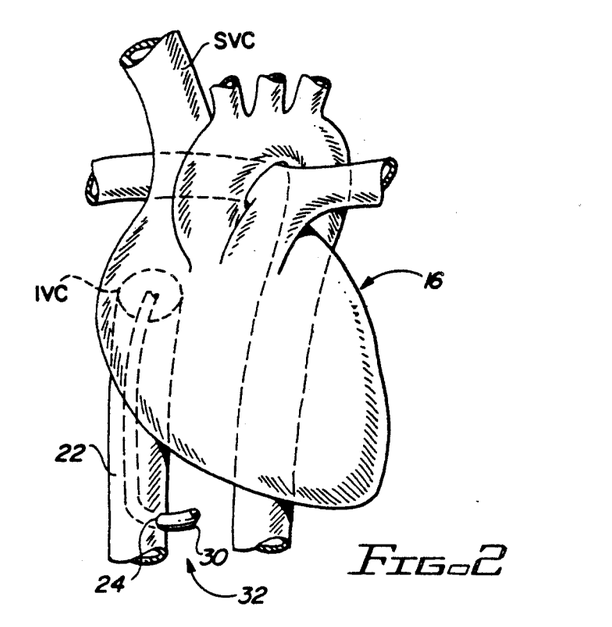
FIG. 2 is a pictorial representation of the heart of FIG. 1 and illustrates the approach to the heart via an IVC access site.

Referring next to FIG. 2, the manner of gaining access to the heart via the IVC is illustrated. Anatomically, the IVC 22 comes through the diaphragm (not shown in FIG. 2) and runs right by the right ventricle (RV) and connects to the right atrium (RA) of the heart 16. Hence, there is virtually no closer access to the pericardium and epicardium than through the IVC. As seen in FIG. 2, an introducer 30 may be transvenously passed through the IVC, through an opening 24, in the wall of the IVC, and into the chest cavity 31. Advantageously, the point where the introducer 30 enters the chest cavity 31 is in close proximity to the right ventricle of the heart. In fact, the typical human anatomy places an object emerging from the medial side of the IVC so as to be abutted against the high right ventricular free wall (a bit dorsally). It is thus a relatively simple procedure to pass the lead through the introducer into the chest cavity 31, position the electrode at a desired location on the heart, and then remove the introducer, leaving the lead and electrode in place.

The hole 24 in the IVC wall is made using the same method described in the above incorporated-by-reference patent application, "Method For Transvenous Implantation of Objects into the Pericardial Space of Patients," for perforating the atrial wall in order to gain access to the pericardial space. That is, a suitable catheter having active fixation means at its distal end is inserted into the IVC and affixed to the wall of the IVC at the desired location where the hole 24 is to be made. This desired location may be determined, at least in part, by controlling the length of the catheter. A guide wire is then inserted through the catheter until a tip of the guide wire makes contact with the wall of the IVC. The tip of the guide wire is then pushed through IVC wall, thereby creating the hole 24. This hole 24 can be easily dilated to pass through other leads or implements, as required. For pericardial placement of an electrode on the right ventricle, the lead having the electrode can be simply passed through the catheter and attached to the heart. For pericardial placement of one or more electrodes on or near the left ventricle, it may be desirable to first insert a suitable introducer 30 through the hole 24, as shown in FIG. 2, and route the introducer 30 within the chest cavity 31 until it is near the desired location on the heart where the electrode is to be placed. In any event, once the hole 24 has been made in the IVC wall, and the lead 18 or introducer 30 inserted therethrough, the placement of the electrode(s) on the heart is readily carried out using techniques described in the referenced documents and known in the art.

Once access has been gained into the chest cavity 31 (mediastinum) via the access hole 24, there are basically two choices for lead positioning from this access site. These choices are: (1) extrapericardial or (2) intra-pericardial. Some patients may have either no pericardium or an abundance of adhesions within the pericardium. For such patients, intra-pericardial positioning is not an option. However, most patients have a pericardium, and the lead may be positioned either extra-pericardially or intra-pericardially. The extra-pericardial positioning will be described first.

Figure 3:
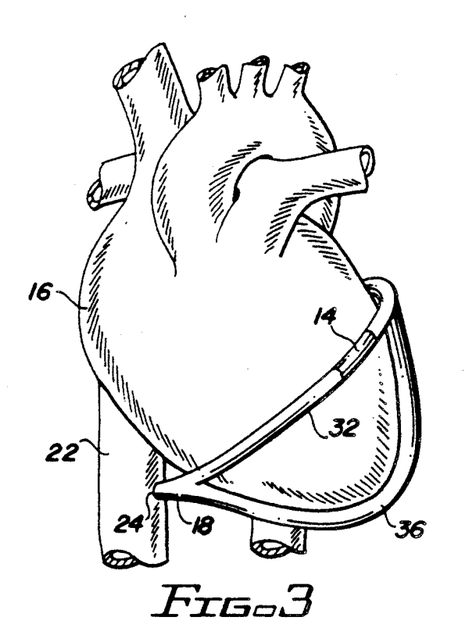
FIG. 3 is a representation of the heart as in FIG. 2 and illustrates one embodiment of a defibrillation lead and electrode(s) that is positioned around the heart as accessed from the IVC access site in accordance with the teachings of the present invention.

Referring to FIGS. 3–6, various configurations are shown for extra-pericardial placement of lead positioning about the heart 16. In FIG. 3, for example, the distal end of the lead 18 loops around the heart and pericardium like a ring or a cup. One branch 32 of the lead loops around the heart, while another branch 36 loops under the heart, thereby forming, in effect, a basket in which the heart is placed. One or more electrodes may be included along the length of the distal end of the lead 18 in order to contact desired areas of the heart. For example, as shown in FIG. 3, the electrode 14 is closest to the left ventricle, which is a preferred location for a defibrillation electrode for many patients. Other electrodes could also be employed to contact other areas of the heart, either on the branch 32 or the branch 36. Alternatively, the entire distal end of the lead 18, including the branches 32 and 36, could include exposed conductive surfaces, thereby forming a "basket electrode" that makes multiple contact with the heart.

Once the lead and electrodes have been deployed to a desired location about the heart, conventional fixation means may be employed in order to anchor the electrodes to their desired position. To avoid puncturing coronary arteries during the lead deployment and fixation process, a sub-xiphoid or intercostal endoscope or a coronary angiography may be utilized.

Figure 4:
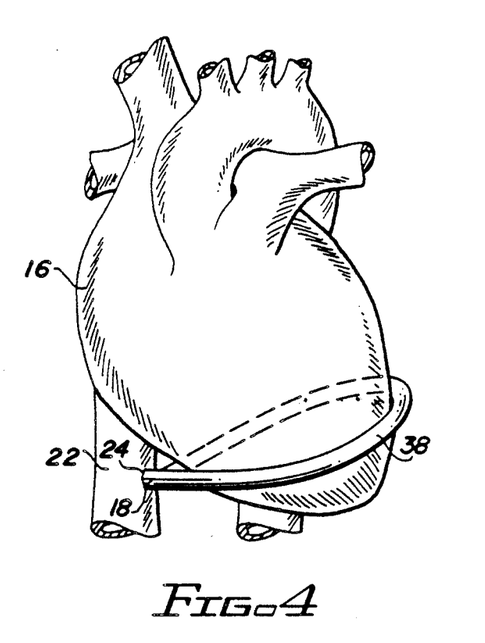
FIG. 4 is a representation as in FIG. 3 and shows an alternative arrangement wherein the distal end of the defibrillation lead and electrode(s) are looped around the ventricles of the heart.

The lead deployment shown in FIG. 4 is similar to that shown in FIG. 3 except that only a single branch 38 of the lead 18 loops around the heart 16. In this case, the loop 38 is positioned lower on the heart 16 than is the loop 32 in FIG. 3, thereby positioning the electrode(s) included as part of the loop 38 over a different region of the ventricles than does the deployment configuration of FIG. 3.

Figure 5:
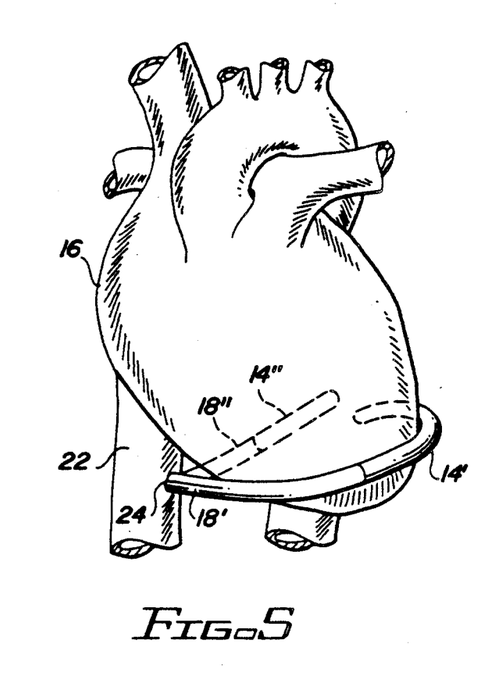
FIG. 5 illustrates another embodiment of the invention using separate non-branching leads to access both the right and left ventricles of the heart through the IVC access site.

In FIG. 5, two separate leads 18' and 18" exit the IVC access hole 22 and contact the heart. The lead 18' includes at least one electrode 14', positioned near the left ventricle of the heart; and the lead 18" includes at least one electrode 14" positioned near the right ventricle of the heart. As with the other lead deployment configurations, fixation means may be used to help anchor the electrodes to the desired tissue locations about the heart.

Figure 6:
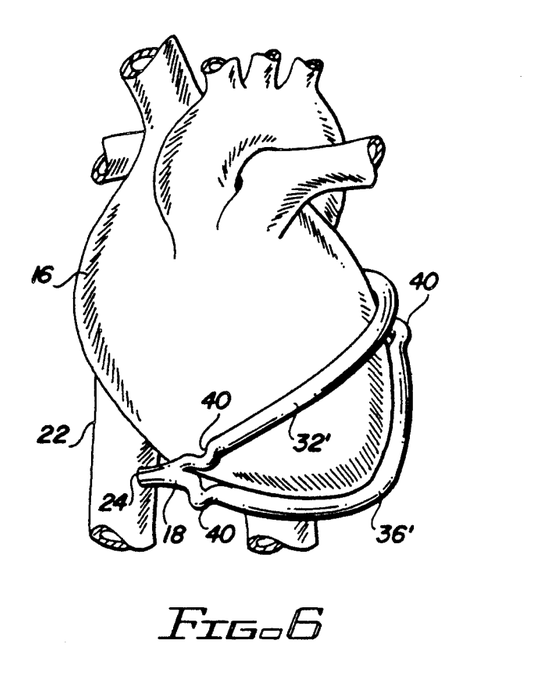
FIG. 6 illustrates an embodiment of the invention wherein the distal portion of the lead wrapped around the heart is made with extra length so that it can hinge as the heart beats.

To limit the stress on the heart, a lead configuration such as is shown in FIG. 6 may be employed. This configuration is similar to that shown in FIG. 3 except that the lead branches 32' and 36' are made from flexible sections 40 and stiff sections (intermediate the flexible sections). Further, the overall length of the branches is somewhat longer than that of the corresponding branches in FIG. 3, with the extra length being taken up in the flexible sections 40. The flexible sections function as pseudo hinges, allowing the stiff sections to move or bend with the heart as the heart beats, rather than stretching.

Figure 7:
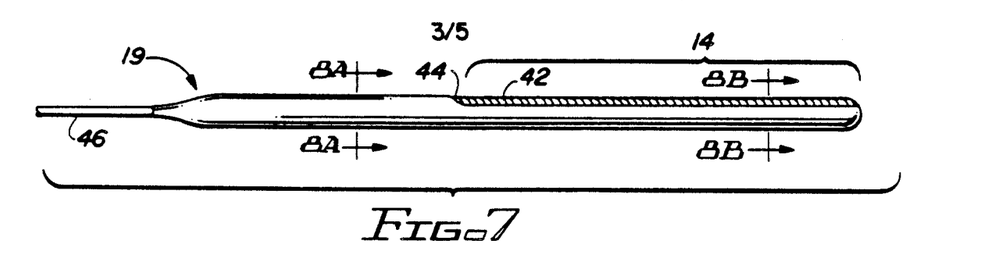
FIG. 7 depicts one embodiment of a defibrillation lead used with the present invention.
Figure 8A:
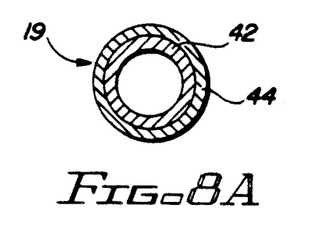
FIG. 8A is a sectional view taken along the line 8A—8A of the lead of FIG. 7.
Figure 8B:
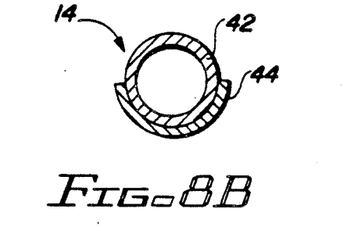
FIG. 8B is a sectional view taken along the line 8B—8B of the lead of FIG. 7.

Referring next to FIG. 7, a representation of one embodiment of a defibrillation lead 19 is illustrated. Sectional views of the lead 19 are depicted in FIGS. 8A and 8B. In many respects, the lead 19 resembles a pacing lead used with implantable pacemakers. The conductor of the lead is preferably a helically wound wire 42 made from a suitable metal alloy that provides for good conductivity and that is compatible with body fluids. Use of a helically wound wire allows the lead to be very flexible, like a spring. Further, the center of the helically wound conductor provides a lumen in which a guiding stylet, or equivalent device, may be removably inserted to help steer the lead to its desired location. If two or more electrically insulated electrodes are desired on the same lead, two or more conductors, each separated by an electrically insulating layer, may be helically wound coaxially, each having a different winding radius than the others. Alternatively, the conductors may be placed side-by-side, separated by an appropriate electrically insulting medium, and helically wound on a common radius.

Figures 9, 10:
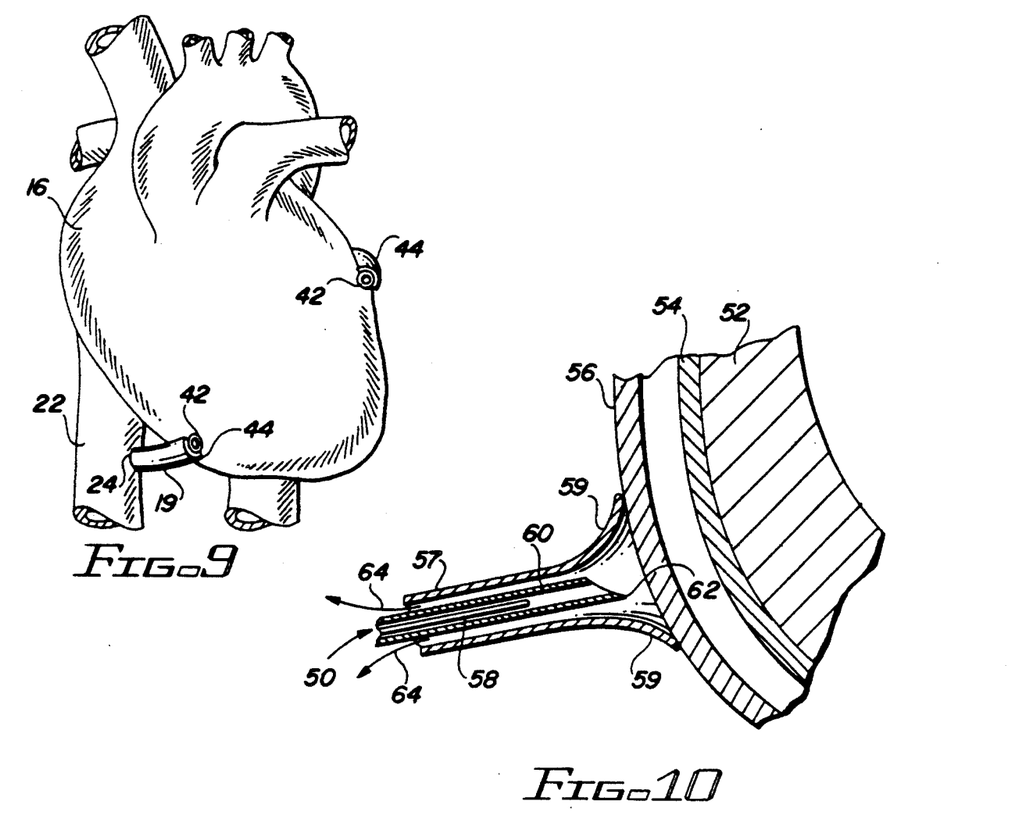
FIG. 9 illustrates a preferred positioning of the lead of FIG. 7 about the heart.
FIG. 10 illustrates one manner in which the pericardium surrounding the heart can be pierced in accordance with the intra-pericardial placement of defibrillation electrodes of the present invention.

The conductor 42 is surrounded by an appropriate electrical insulator sheath 44, made from a body compatible material such as silicone rubber. One end of the conductor 42 is connected to a proximal connector 46. The proximal connector 46 is configured for detachable placement within a suitable defibrillation device 12 (FIG. 1). The other end of the lead 18 includes the electrode(s) 14. In the embodiment shown, the electrode 14 is realized by simply exposing a length of the helically wound conductor 14 around roughly ½ of the circumference of the lead. In this fashion, the distal end of the lead 19, including the electrode 14, can easily be maneuvered through the opening 24 in the wall of the IVC 22 to its desired cardiac location. Furthermore, as shown in FIG. 9, which shows in partial sectional view the lead 19 deployed about the heart 16, the electrode 14 (the exposed half of the conductor 42) may be oriented to face towards the heart 16, thereby directing and concentrating the defibrillation energy towards the heart, and limiting such energy from being directed away from the heart.

Where intra-pericardial placement of the defibrillation electrodes is desired, it is first necessary to create an access hole 24 in the IVC as described above. Once this hole is made, it is dilated and a sheath, such as the sheath 30 shown in FIG. 2, is left in place and guided to a location near the pericardium at which the pericardium is to be pierced. This sheath provides a convenient mechanism for introducing and directing various implements to the heart.

One such implement is a tool 50 used to perforate the pericardium while sparing the myocardium. Such a tool is illustrated in FIG. 10, wherein an enlarged view of the myocardium 52, epicardium 54 and pericardium 56 is illustrated. The tool 50 includes a sheath or catheter 57 (which may comprise the same sheath 30 left in place after creating the IVC hole 24) having a soft catheter tip 59. Inside the catheter 57 is a hollow needle 60 having a sharpened tip 62. A guide wire 58 is inserted through the lumen of the needle 60. This needle may be retractable and extendable. This lumen may also be used for infusion and/or drainage of fluids used in the intra pericardial placement process. The other end of the sheath 30 is connected to a vacuum source (not shown), which vacuum source applies suction forces in the direction shown by the arrows 64.

In operation, the sharp tip 62 of the needle 60 cannot advance past the end of the catheter 59. When suction is applied to the other end of the catheter 59, the pericardium 56 is pulled into the catheter tip and impaled on sharp tip 62, thereby cutting through the tissue. Next, while suction is maintained in the outer lumens, as indicated by the arrows 64, a fluid may be infused through the center lumen. The use of this fluid is optional, but if used, it distends the pericardium 56 away from the epicardium 54, thereby facilitating the subsequent insertion of the guide wire 58 into the pericardial space. (The pericardial space is that space between the epicardium and the pericardium.) The guide wire 58 is placed through the impaled hole, and the hole is dilated using conventional means. The dilation is facilitated by the infusion of the fluid. Alternative embodiments may include means for extending the sharpened tip 62 a sufficient distance to penetrate the pericardium, but not far enough to penetrate the atrial wall.

Once the hole in the pericardium has been enlarged sufficiently, the catheter 59 may be removed and replaced with an introducer. The dilator is then removed leaving the introducer sheath in place. The procedure for inserting the lead and electrode through the introducer sheath and the pericardial hole into the pericardial space is the same as described in the previously referenced documents (incorporated by reference herein) for atrial perforation access to the pericardium.

It is noted that the pericardial hole, as well as the access hole 24 in the IVC 22, may be sealed using any of the techniques described in the referenced documents for sealing the hole in the atrial wall, although for most patients, such sealing should not be necessary as the body of the lead that passes through such holes will itself function to stop any significant leakage through these holes at the relatively low pressures encountered.

Figure 11A:
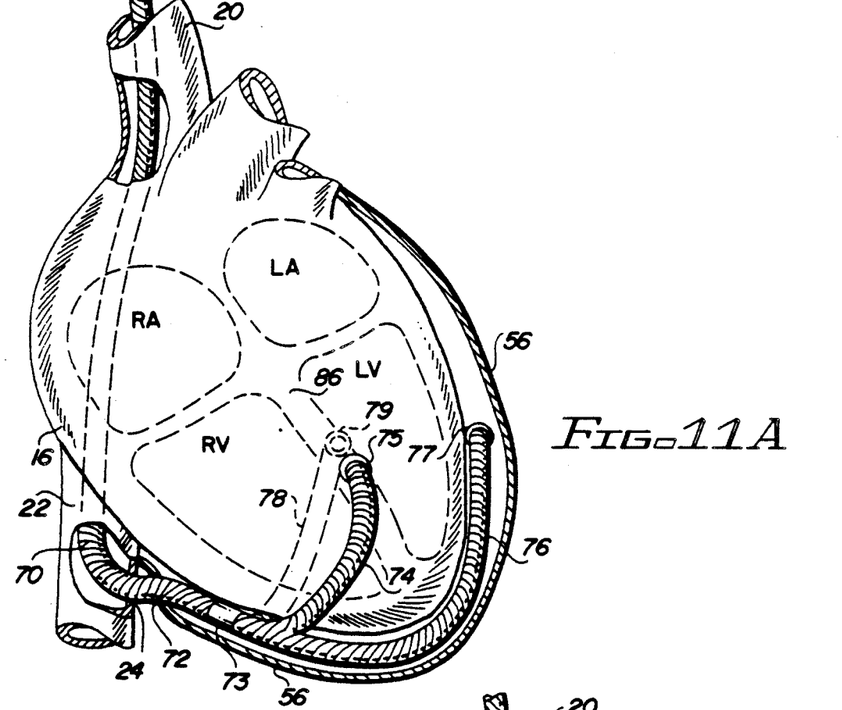
FIGS. 11A, 11B and 11C illustrate respective intra-pericardial placement of electrodes about the heart in accordance with the teachings of the present invention, with FIGS. 11B and 11C including the use of endocardial defibrillation electrodes.
Figure 11B:
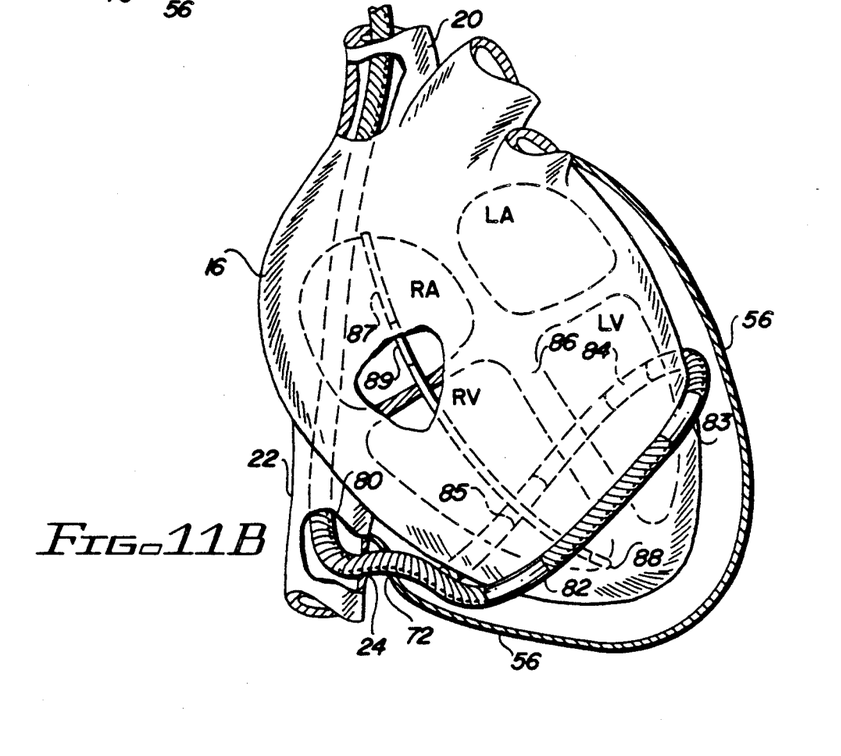
Figure 11C:
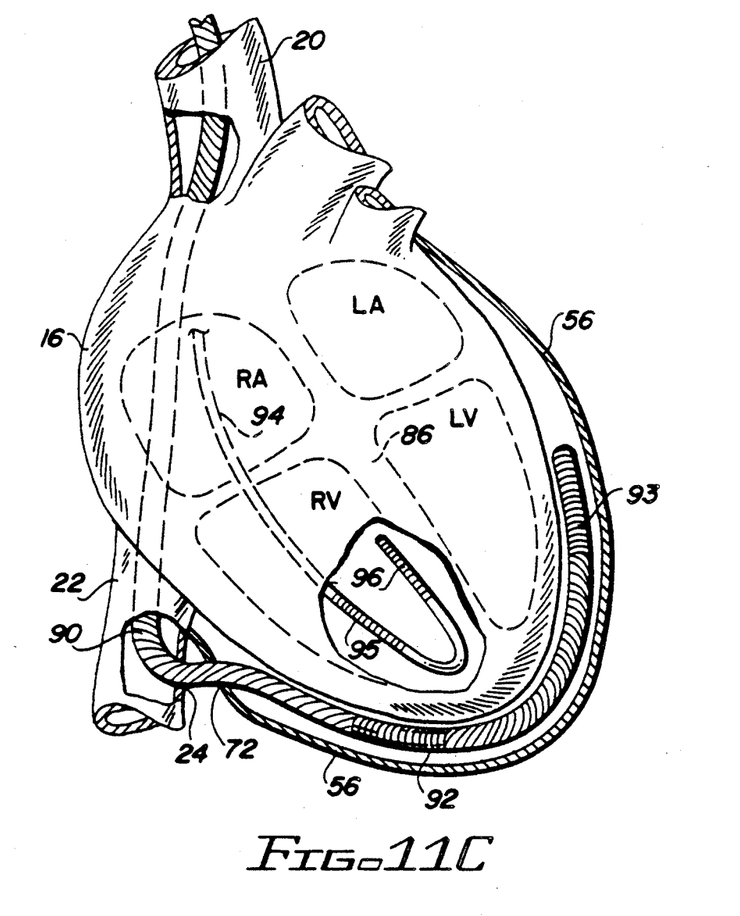

Referring next to FIGS. 11A–11C, representative intra-pericardial lead deployments and electrode placements used with the present invention are depicted in simplified form. In FIG. 11A, a defibrillation lead 70 passes through an opening 24 in the IVC 22, through a pericardial hole 72, and into the pericardial space between the heart 16 and the pericardium 56. Both the IVC hole or opening 24 and the pericardial hole or opening 72 may be made in the manner described above. The distal tip of the lead 70 includes three branches 74, 76 and 78. Each branch includes an electrode 75, 77, and 79 at its respective end. An additional electrode 73 is included on the lead 70 prior to the junction point of the branches 74, 76 and 78. Advantageously, this electrode placement provides efficient coverage of both the right and left ventricular tissue, particularly where the electrodes 77 and 73 are charged to a defibrillation potential of one polarity, and the electrodes 75 and 79 are charged to a defibrillation potential of the opposite polarity.

FIG. 11B illustrates another intrapericardial defibrillation lead deployment used in conjunction with an endocardial defibrillation lead deployment. In FIG. 11B, an IVC hole 24 and pericardial hole 72 are made as described previously. A lead 80 is inserted through both of these holes and looped around the epicardial tissue of the heart so as to be about the right and left ventricles of the heart. This lead 80 includes electrodes 82, 83, 84 and 85 spaced apart on the loop encircling the heart. For the particular embodiment shown in FIG. 11B, electrodes 82 and 85 are in close proximity to opposing walls of the right ventricle (RV), and electrodes 83 and 84 are in close proximity to opposing walls of the left ventricle (LV). Other intra-pericardial electrode placements could also be used as needed for a particular patient. (For example, electrodes 82 and 84 could be positioned nearest the septum 86 separating the left and right ventricles, electrode 83 could be positioned on an opposing wall of the left ventricle, and electrode 85 could be positioned on an opposing wall of the right ventricle.) An endocardial lead 87, including an electrode 88 near or at its distal tip, is also inserted into the right ventricle of the heart in conventional manner. Preferably, the electrode 88 is positioned near the right ventricular apex. During defibrillation, the intra-pericardial electrodes 82–85 are energized with a defibrillation potential of one polarity, and the endocardial electrode 88 is charged with a defibrillation potential of the opposite polarity. Electrical current thus flows between the oppositely charged electrodes through myocardial tissue, thereby triggering the desired depolarization of such tissue.

As shown in FIG. 11B, an additional endocardial electrode 89 may be included on the lead 87 and positioned within the right atrium (RA) of the heart. This arrangement of endocardial defibrillation electrodes advantageously directs the defibrillation current to both ventricular and atrial myocardial tissue, which distribution of defibrillation current may be preferred for some patients. Further, it is noted that while the simplest manner of using the electrodes shown in FIG. 11B is to charge the intra-pericardial electrodes to one potential and the endocardial electrodes to another potential, it may be preferred to utilize a lead construction that allows each electrode to be charged to a separate potential. With such an arrangement, a desired sequence of defibrillation potentials can be applied between respective ones of the electrodes so as to more effectively control the distribution of the defibrillation current to specific myocardial tissue.

Referring to FIG. 11C, yet another defibrillation lead deployment system is shown using both an intra-pericardial lead 90 and an endocardial lead 94. The lead 90 passes through an opening 24 in the IVC 22 and into the pericardial space through an opening 72 in the pericardium 56 as described above. Once in the pericardial space, the lead is routed about the apex of the heart. An electrode 92 contacts epicardial tissue proximate the right ventricle and an electrode 93 contacts epicardial tissue proximate the left ventricle. The endocardial lead 94 includes two electrodes 95 and 96 that preferably both contact the septum 86. (As shown in FIG. 11C, only the electrode 96 appears to be in contact with the septum 86. However, electrode 95 may also be in contact with a different portion of the septum than is electrode 96, and is shown spaced away from the septum only to emphasize that there are two endocardial electrodes included in the right ventricle.)

Numerous other electrode and lead deployment arrangements are contemplated, both for intra-pericardial, extra-pericardial, and/or endocardial placements. That which is illustrated in the figures is only intended to be representative.

While the invention described herein has been described with reference to particular embodiments and applications thereof, numerous variations and modifications could be made thereto by those skilled in the art without departing from the spirit and scope of the invention. Various features of the invention are set forth in the claims below.

What is claimed is:

1. A method of transvenously implanting a defibrillation lead about a mammalian heart; said heart being located within a chest cavity, said heart having a major vein proximate thereto, said defibrillation lead having at least one distal electrode, a flexible body, and proximal connection means for making electrical contact with the distal electrode from a proximal end of the lead; said method comprising the steps of:
   (a) transvenously inserting guide means into the chest cavity from a position within said major vein;
   (b) inserting the distal electrode of the defibrillation lead into the chest cavity following said guide means; and
   (c) positioning said distal electrode within the chest cavity so as to be about said heart.

2. The method of claim 1 wherein step (a) of transvenously inserting guide means into the chest cavity comprises:
   (1) identifying an access site to said chest cavity from within said major vein,
   (2) making a first hole through the wall of said major vein at said access site, and
   (3) passing said guide means through said major vein and into the chest cavity through said first hole.

3. The method of claim 2 wherein the step of identifying said access site comprises inserting a catheter into said major vein a prescribed distance from a known reference location; and affixing a distal end of said catheter to the inner wall of said major vein once it has been inserted into the major vein said prescribed distance, the point at which the distal end of said catheter is affixed to said major vein comprising said access site.

4. The method of claim 3 wherein the step of making the first hole through the wall of the major vein at the access site comprises inserting a stylet having a sharpened tip through said catheter until said tip contacts the wall of the major vein at the access site; and forcing the tip of said stylet through said wall.

5. The method of claim 4 further including the step of enlarging the first hole sufficiently to allow the defibrillation electrode and distal electrode to pass therethrough.

6. The method of claim 1 wherein step (c) of positioning the distal electrode about the heart comprises looping the distal portion of the defibrillation lead containing said at least one electrode around the pericardium that surrounds the heart.

7. The method of claim 6 wherein the step of looping the distal portion of the defibrillation lead around the pericardium includes positioning said loop so that said at least one electrode is proximate one of the ventricles of the heart.

8. The method of claim 1 wherein step (c) of positioning the distal electrode about the heart comprises inserting a distal portion of the defibrillation lead containing said at least one electrode into the pericardial space surrounding the heart.

9. The method of claim 8 wherein the step of inserting the distal portion of the defibrillation lead into the pericardial space comprises making a second hole in the pericardium from a position accessible from said chest cavity; inserting said guide means from said major vein through said chest cavity and into the pericardial space through said second hole; and inserting a distal portion of the defibrillation lead, including said at least one electrode, into the pericardial space following said guide means.

10. A method of implanting a defibrillation lead about the heart of a patient, said defibrillation lead having at least one exposed conductive surface near its distal end that serves as an electrode, said method comprising the steps of:
   (a) accessing the inferior vena cava (IVC) of the patient;
   (b) making a first small hole in said IVC at a location proximate the heart of the patient;
   (c) inserting the distal end of said defibrillation lead through said first small hole; and
   (d) positioning the electrode of said defibrillation lead about the heart of the patient.

11. The method of claim 10 wherein step (d) of positioning the electrode about the heart of the patient comprises positioning the electrode extrapericardially about the heart of the patient.

12. The method of claim 11 wherein the step of positioning the electrode of said defibrillation lead about the heart includes looping the distal end of the lead around those portions of the heart proximate the ventricles of the heart, whereby the electrode is positioned so as to be in close proximity to ventricular myocardial tissue.

13. The method of claim 12 wherein the electrode of said defibrillation lead is exposed only around a portion of the circumference of said lead at the location on said lead where said electrode is positioned, and wherein the step of looping the lead around said heart includes positioning said exposed electrode so that it faces inwardly towards the heart.

14. The method of claim 10 wherein step (d) of positioning the electrode about the heart of the patient comprises positioning the electrode intrapericardially about the heart of the patient.

15. The method of claim 14 wherein step (d) comprises:
   (1) making a second small hole in the pericardial tissue surrounding the heart of the patient from a position accessible from said first small hole in the IVC; and
   (2) inserting the distal end of said defibrillation lead through said second small hole so that said second electrode lies within the pericardial space about said heart.

16. The method of claim 15 wherein the step of making a second small hole in the pericardial tissue comprises:
   inserting a catheter through said small first hole until a distal tip thereof contacts pericardial tissue surrounding said heart, said catheter including retracted cutting means therein for making a hole in body tissue that makes contact therewith; and extending said tissue cutting means to contact said pericardial tissue, thereby making said second small hole in the pericardial tissue surrounding the heart.

17. The method of claim 15 wherein the step of making a second small hole in the pericardial tissue comprises:

inserting a catheter through said small first hole until a distal tip thereof contacts pericardial tissue surrounding said heart, said catheter including tissue cutting means therein for making a hole in body tissue that makes contact therewith; and forcing the pericardial tissue into the distal tip of said catheter until said tissue makes contact with said tissue cutting means, thereby making said second small hole in the pericardial tissue surrounding the heart.

18. The method of claim 17 wherein the step of forcing the pericardial tissue into the distal tip of said catheter comprises attaching a proximal end of said catheter to a vacuum source, and applying suction forces with said vacuum source that pull said pericardial tissue into the distal tip of said catheter.

19. A method of positioning at least one defibrillation electrode about the heart of a mammal, said heart being contained within pericardial tissue, said pericardial tissue having an inner layer adjacent epicardial tissue of said heart, and an outer layer facing away from said heart, said method including:

inserting said at least one electrode through a vein that passes proximate said heart;

routing said at least one electrode through an access site in a wall of said vein to an adjacent chest cavity, said pericardial tissue being located within said chest cavity; and positioning said at least one electrode within said chest cavity so as to make contact with said pericardial tissue.

20. The method set forth in claim 19 wherein the step of positioning said at least one electrode within said chest cavity comprises extra-pericardial positioning of said at least one electrode, said at least one electrode thereby making contact with the outer layer of said pericardial tissue.

21. The method set forth in claim 19 wherein the step of positioning said at least one electrode within said chest cavity comprises intra-pericardial positioning of said at least one electrode, said at least one electrode thereby making contact with the inner surface of said pericardial tissue and the epicardium of said heart.

22. The method set forth in claim 21 wherein said intra-pericardial positioning of said at least one electrode comprises: piercing said pericardial tissue from a position within said chest cavity so as to make a passageway therethrough; passing said at least one electrode through said passageway; and positioning said at least one electrode at a desired location between the epicardium and the inner layer of said pericardial tissue.

23. A system for implanting a defibrillation lead in a mammal, said mammal having a heart surrounded by a pericardium, said defibrillation lead having at least one flexible elongate electrode near a distal end thereof, said system comprising:

guide means for transvenously gaining direct access to a chest cavity of said mammal, said heart and pericardium being located within said chest cavity, said direct access passing directly from an access site in a wall of a vein proximate said chest cavity to the chest cavity without passing through said heart;

means for inserting the distal end of said electrode, including said at least one electrode, into said chest cavity following said guide means; and means for positioning said at least one electrode within said chest cavity about said heart.

24. The system for implanting a defibrillation lead as set forth in claim 23 wherein said means for positioning said at least one electrode about said heart comprises means for positioning said at least one electrode so as to make contact with said pericardium.

25. The system for implanting a defibrillation lead as set forth in claim 23 wherein said means for positioning said at least one electrode about said heart comprises means for positioning said at least one electrode so as to make contact with the epicardium, or outer layer, of said heart.

26. The system for implanting a defibrillation lead as set forth in claim 25 wherein said means for positioning said at least one electrode about said heart further includes means for piercing said pericardium, said at least one electrode passing through said pericardium so as to make direct contact with the epicardium of the heart.

27. The system for implanting a defibrillation lead as set forth in claim 23 wherein the means for positioning the distal end of said lead about said heart includes means for looping a distal portion of said lead around said heart.

28. The system for implanting a defibrillation lead as set forth in claim 27 wherein the distal portion of said lead includes stiff sections and flexible sections, and wherein said means for looping a distal portion of said lead around said heart includes means for looping said lead around said heart so that the stiff sections hold the looped lead in place against the heart, and the flexible sections bend as the heart contracts and expands.

29. A defibrillation lead system comprising:

a sheath;

means for passing said sheath through to a pericardium surrounding a heart from a position within the inferior vena cava (IVC) adjacent said heart;

a defibrillation lead having a distal electrode, said defibrillation lead being of a size that allows it to be slidably inserted through said sheath until said distal electrode is in contact with the pericardium; and holding means for holding said distal electrode in contact with the pericardium.

30. The defibrillation lead system of claim 29 wherein said holding means comprises means for holding the distal electrode in contact with the outside of said pericardium.

31. The defibrillation lead system of claim 30 wherein said holding means comprises stiff and flexible sections of the distal end of said defibrillation lead, said stiff sections being formed to encircle and conform with the basic shape of the heart, said flexible sections being formed to readily bend as said heart contracts and expands, whereby the stiff sections maintain contact with the contracting and expanding heart without having to stretch.

32. The defibrillation lead system of claim 29 wherein said holding means comprises means for holding the distal electrode in contact with epicardial tissue inside of said pericardium.

33. The defibrillation lead system of claim 29 wherein said distal electrode comprises an exposed conductive element that is substantially flush with the body of said lead.

34. The defibrillation lead system of claim 33 wherein said conductive element is exposed only around a portion of the circumference of said lead body, whereby said exposed conductive element may be selectively positioned relative to the cardiac tissue in order to make direct contact with desired tissue.

* * * * *